(12) United States Patent
Heikenfeld et al.

(10) Patent No.: US 11,609,163 B2
(45) Date of Patent: Mar. 21, 2023

(54) DEVICES AND METHODS FOR PROCESSING FLUID SAMPLES

(71) Applicant: University Of Cincinnati, Cincinnati, OH (US)

(72) Inventors: Jason Charles Heikenfeld, Cincinnati, OH (US); Andrew Jajack, North Canton, OH (US); Eliot Gomez, Cincinnati, OH (US); Michael Charles Brothers, Lebanon, OH (US); Isaac Stamper, Morrow, OH (US)

(73) Assignee: University Of Cincinnati, Cincinnati, OH (US)

( * ) Notice: Subject to any disclaimer, the term of this patent is extended or adjusted under 35 U.S.C. 154(b) by 333 days.

(21) Appl. No.: 16/642,184

(22) PCT Filed: Aug. 30, 2018

(86) PCT No.: PCT/US2018/048809
§ 371 (c)(1),
(2) Date: Feb. 26, 2020

(87) PCT Pub. No.: WO2019/046557
PCT Pub. Date: Mar. 7, 2019

(65) Prior Publication Data
US 2020/0200655 A1 Jun. 25, 2020

Related U.S. Application Data
(60) Provisional application No. 62/551,826, filed on Aug. 30, 2017.

(51) Int. Cl.
*G01N 1/40* (2006.01)
*G01N 27/447* (2006.01)
*G01N 33/58* (2006.01)

(52) U.S. Cl.
CPC ......... *G01N 1/40* (2013.01); *G01N 27/44704* (2013.01); *G01N 33/582* (2013.01)

(58) Field of Classification Search
CPC ....... B01J 19/0086; C12M 33/00; G01N 1/40; G01N 1/4005; G01N 1/4077;
(Continued)

(56) References Cited

U.S. PATENT DOCUMENTS 6,306,660 B1* 10/2001 Messenger ............. G01N 33/52
436/15
2012/0267307 A1* 10/2012 McGinnis ............... C02F 1/445
210/321.64
2018/0348164 A1* 12/2018 Kimani ................ G01N 1/4005

FOREIGN PATENT DOCUMENTS

WO 2009120642 A1 10/2009
WO 2010011760 A1 1/2010
(Continued)

OTHER PUBLICATIONS

International Search Report and Written Opinion in International Patent Application No. PCT/US2018/048809, dated Nov. 16, 2018, 11 pgs.

*Primary Examiner* — Maureen Wallenhorst
(74) *Attorney, Agent, or Firm* — Wood Herron & Evans LLP (57) ABSTRACT

Described are devices for and methods of modulating a fluid sample. The devices (10, 40, 60, 80, 100, 130, 160, 220) include at least one sample-modulating component (20, 76, 78, 90, 110, 112, 116, 150, 152, 154, 162, 164, 182, 184, 186, 222, and 230) and, in some embodiments, two or more sample-modulating components. The sample-modulating components are each capable of performing a function selected from the following group: concentrating the sample to increase a concentration of a first constituent of the sample; diluting the sample to decrease a concentration of a (Continued)

second constituent in of the sample; desalinating the sample to decrease the total moles of salt in the sample volume or causing a temporary decrease in the osmolarity; adjusting pH of the sample to bring a pH of the sample into a predetermined range; absorbing one or more nonpolar substances to decrease a concentration of the nonpolar substances; and delivering one or more reagents to the sample to provide a desired concentration of the reagent in the sample.

3 Claims, 10 Drawing Sheets

(58) Field of Classification Search
CPC ....... G01N 27/44704; G01N 27/44791; G01N 33/54366; G01N 33/582; Y10T 436/11; Y10T 436/115831; Y10T 436/117497; Y10T 436/12; Y10T 436/25; Y10T 436/255; Y10T 436/2575
USPC .... 436/43, 50, 52, 55, 63, 20, 39, 174, 178, 436/180; 422/63, 67, 68.1, 81, 527, 535
See application file for complete search history.

(56) References Cited

FOREIGN PATENT DOCUMENTS

| WO | 2011011669 A1 | | 1/2011 |
|---|---|---|---|
| WO | 2013/019812 | * | 2/2013 |
| WO | 2017070640 A1 | | 4/2017 |
| WO | 2017070641 A1 | | 4/2017 |

* cited by examiner

DEVICES AND METHODS FOR PROCESSING FLUID SAMPLES

STATEMENT REGARDING FEDERALLY SPONSORED RESEARCH OR DEVELOPMENT

This invention was made with Government support under ECCS-1608275 awarded by the National Science Foundation. This invention was made with Government support under U.S. Government contract No. FA8650-16-C-6760 awarded by the Air Force Materiel Command from the Air Force Research Laboratory of the Department of the Air Force. The Government has certain rights in this invention.

BACKGROUND

There are many applications where fluid samples must be processed before analysis including but not limited to biofluid samples, water samples, such as waste water, municipal water, environmental sources, as well as food processing samples. For example, biofluid samples, including but not limited to, blood, functions of blood, sweat, saliva, tears, and urine often contain components such as salts, lipids, acids/bases, proteins (e.g. glycoproteins), sugars, enzymes and other interfering components that must be removed or modified before analytes can be measured. Salt concentrations are particularly important for biosensors such as aptamers, antibodies, and enzymes since biomolecules can precipitate when salt concentrations are low (e.g., <10 mM osmolarity) or when salt concentrations are high (e.g., >1 M osmolarity). Salt concentrations are also known to impact binding affinity, with higher salt concentrations often times leading to reduced analyte binding due to shielding of charges. Lipids may foul analyte biosensors or cause non-specific binding. Analyte biosensors, such as enzyme-based biosensors work best within an optimal pH range, usually around pH 7. In addition, the range of the concentration of the analyte in these biofluids under physiological conditions may be above or below the sensitivity range of the sensors.

The objects and advantages of the disclosed invention will be further appreciated in light of the following detailed descriptions and drawings.

SUMMARY

To overcome these challenges, embodiments of the present invention include devices and methods that process fluid samples using one or more processing stages or components that perform the following functions: concentration, dilution, desalination or salination, pH buffering, scrubbing of nonpolar substances (lipids and detergents), reagent delivery for processes that require reagents (e.g., ELISAs), and heating or cooling of the fluid samples. These methods and devices may also be useful in environmental monitoring applications. Fluid samples may include biofluid samples, water samples, and food processing samples for pollutants, contaminants, toxins, bacteria/algae growth, or combinations thereof. The method and devices may also be useful in monitoring fluid food processing samples where allergens or pathogens must be monitored and where traditional monitoring methods struggle with similar challenges.

Embodiments of the present invention are also directed to continuous flow applications where fluid samples are modified before being used in subsequent steps. In these cases, the fluid sample is not merely sampled but is wholly modified. Exemplary continuous flow applications including chemical processing applications where an in-line system prepares feedstocks prior to downstream reactions. For simplicity, as used herein, a "fluid sample" means either a subset of a larger fluid to be modified prior to sensing and/or as a fluid to be wholly modified for downstream use. The fluid sample may be a biofluid sample including, without limitation, blood, sweat, saliva, tears, and urine. In addition, the fluid sample can be fluid from aquatic sources such as waste water, drinking water, and natural bodies of water. Further, the fluid sample may be a food processing sample. While the embodiments described below are directed to processing biofluid samples, it should be recognized that the embodiments of the disclosed invention may be useful with other fluid samples.

DETAILED DESCRIPTION OF THE INVENTION

One skilled in the art will recognize that the various embodiments may be practiced without one or more of the specific details described herein, or with other replacement and/or additional methods, materials, or components. In other instances, well-known structures, materials, or operations are not shown or described in detail herein to avoid obscuring aspects of various embodiments of the invention. Similarly, for purposes of explanation, specific numbers, materials, and configurations are set forth herein in order to provide a thorough understanding of the invention. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention but does not denote that they are present in every embodiment. Thus, the appearances of the phrases "in an embodiment" or "in another embodiment" in various places throughout this specification are not necessarily referring to the same embodiment of the invention. Further, "a component" may be representative of one or more components and, thus, may be used herein to mean "at least one." As used herein, "sample volume" refers to the volume of sample fluid that directly contacts a sensor. As used herein, "reagents" are not limited to species involved in a chemical analysis or reaction but also include any solute.

Certain embodiments of the disclosed invention show sensors as simple individual elements. It is understood that many sensors require two or more electrodes, reference electrodes, or additional supporting technology or features which are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a biofluid sensor; an impedance sensor; a sample volume sensor; a sample generation rate sensor; and a solute generation rate sensor. Certain embodiments of the disclosed invention show sub-components of what would be sensing devices with more sub-components needed for use of the device in various applications, which are obvious (such as a battery), and for purposes of brevity and focus on inventive aspects, such components may not be explicitly shown in the diagrams or described in the embodiments of the disclosed invention.

Embodiments of the disclosed invention adjust at least one of an analyte concentration, pH, one or more ion concentrations, and an interferent concentration in a fluid sample. In an embodiment, the concentration of an analyte in the fluid sample is increased while the concentration of at least one of the pH, one or more ion concentrations, and one or more interferents, i.e., compounds that would interfere with analyte detection, are adjusted to provide improved conditions for detecting the analyte by a sensor. For example, the pH and ion concentration may be increased or decreased while the concentration of one or more interferents may be decreased. In an exemplary embodiment, a lateral flow assay device, such as a pregnancy test, increases the concentration of the analyte, e.g., a hormone such as human chorionic gonadotropin, while simultaneously adjusting the pH and salt concentration of the sample fluid to improve the binding efficiency of the sensor, and alternatively, decreasing the concentration of one or more interferents.

Embodiments of the disclosed invention are directed to devices capable of salinating or desalinating fluid samples using an applied electric current based on the principle of electrodialysis. In an embodiment, the device includes a membrane layer, electrodes, and an optional reservoir between the electrode and the membrane layer. In an embodiment, the reservoir may contain one or more catalysts or reagents that remove hypochlorite from solution, such as nickel oxide and sodium bisulfite. The membrane layer may be a hydrogel (e.g., polyacrylamide gel (PAM) with or without dopants) or an ion selective membrane. Gels can be either neutral or charged; if charged, the gels will act as an ion selective membrane. Ion selective membranes such as Nation® or electrodialysis membranes may be used. The pore size of the membrane may be tuned to deliver or prevent delivery of different target analytes. The electric potential to be applied depends in part on the pore size. For example, larger pores have less fluidic resistance and, as a result, require a lower potential to induce transport across the membrane. The electrodes can be either in-plane (e.g., on a sidewall) or out of plane. The optional reservoir between the electrode and the membrane layer can contain a salt solution to improve electrical connection, a buffer to prevent corrosion of materials, a low osmolarity solution to improve the thermodynamics of the system, or an equimolar solution to prevent reverse flux. Positive ions (e.g., sodium, potassium, protons) are attracted to the electrochemical cathode. Protons have the greatest electrophoretic flux; thus, the applied electric current naturally removes protons from solution, buffering the pH to about 7 (2 $H^+ + 2\ e^- \rightarrow H_2$ (g)). Negative ions (e.g., chloride, lactate, carbonate, hydroxide) will flux towards the electrochemical anode. Reverse flux is limited by the membrane layer.

Figure 1:
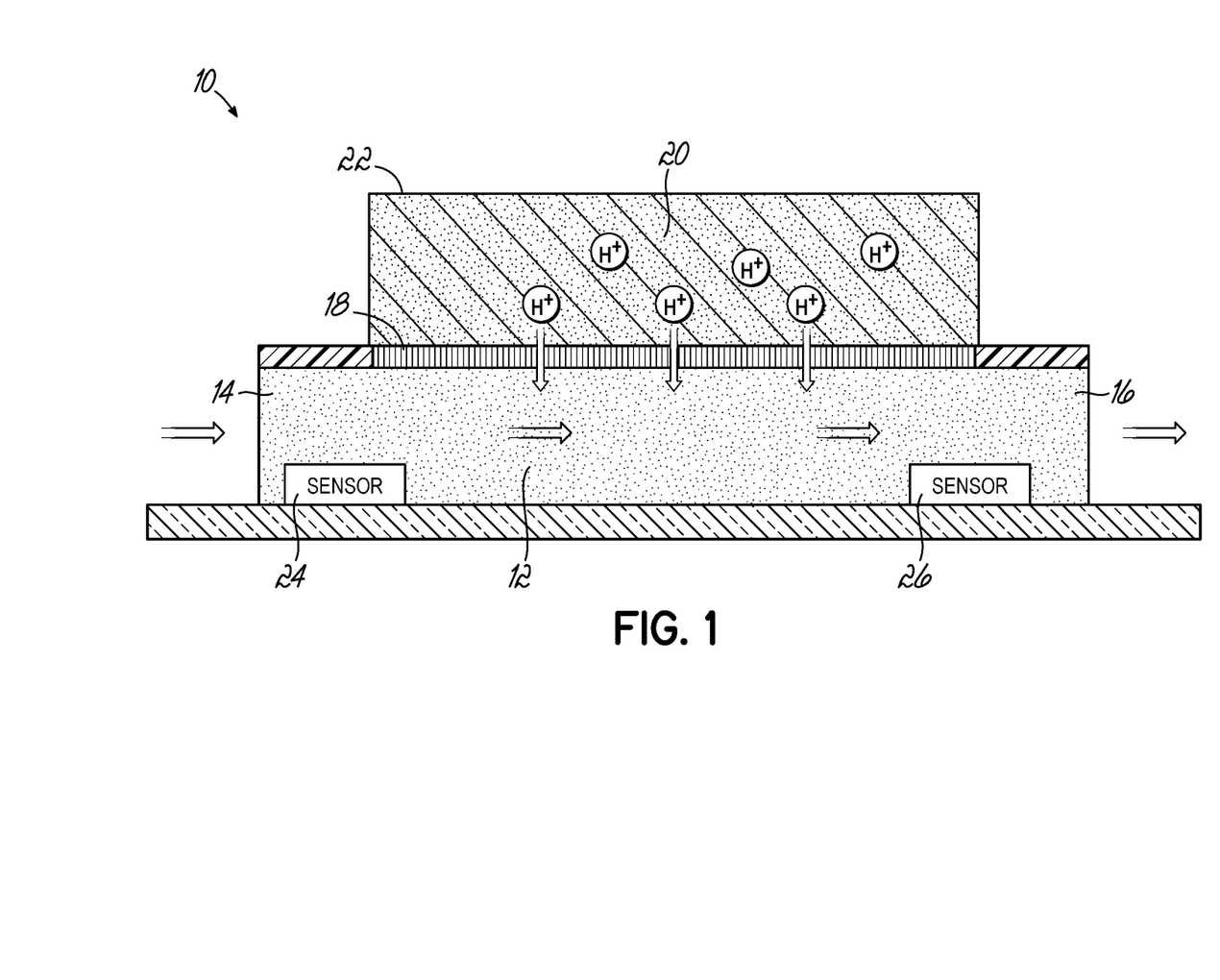
FIG. 1 is a schematic cross-sectional view of a device according to an embodiment of the disclosed invention capable of pH buffering a biofluid sample.

With reference to FIG. 1, in an embodiment, a system 10 is shown that uses osmotic flux to drive dissolved solutes from low to high osmolarity regardless of solute concentration. This can be used to deliver or remove dissolved solutes. Osmosis is the movement of water from low to high osmolarity. At high fluxes, the movement of water through a semipermeable membrane prevents solutes from equilibrating. Instead, dissolved solutes can be carried with the water and driven against their concentration gradient. This process can be used to adjust the pH of the sample by driving a buffer or delivering reagents or other molecules of interest into the sample. In FIG. 1, the device 10 includes a fluid channel 12 having an inlet 14, an outlet 16, and a semipermeable membrane 18 that forms one of the sidewalls. A fluid sample flows through the inlet 14 and across the semipermeable membrane 18 to the outlet 16. The semi-permeable membrane separates a draw solution 20 in reservoir 22 from the channel 12. The draw solution 20 has a lower osmolarity than the sample. This causes an osmotic pressure that pulls both water and a pH buffer ($H^+$) across the semi-permeable membrane 18 into the channel 12, which buffers the pH of the sample. Thus, the pH may be adjusted to be within a predetermined range. The predetermined range may be, for example, the pH range in which a downstream sensor is configured to operate. The ability to buffer pH is important because many sensors 24, 26, such as aptamer-based biosensors, are pH dependent. Buffering pH is also useful in applications where the sample is meant to be used in its entirety after exiting the device such as in food processing or in the production of cosmetic formulations.

The movement of water across a semipermeable membrane is driven by an applied pressure gradient across the membrane. As an example, osmotic pressure is taught herein as the source of the pressure gradient across the membrane. However, other methods of applying a pressure gradient across the membrane exist (e.g., capillary pressure, hydrostatic pressure, etc.). Capillary pressure, or Laplace pressure, is a result of the surface tension of the interface between immiscible fluids. A capillary pressure gradient may be established by placing a material with a high capillary pressure (i.e., wicking pressure) such as paper products, fumed silica, regenerated cellulose, hydrogels, aerogels, etc. Another example of a method of applying a pressure gradient across the membrane is hydrostatic pressure. Hydrostatic pressure gradients may be generated by applying a positive pressure to sample side of the membrane, driving water through the membrane. Hydrostatic pressure gradients may also be generated by applying a negative pressure gradient to the draw side of the membrane. A combination of positive and negative pressure may also be used.

In some cases, reagent delivery as described above may be used to deliver an aptamer, a peptimer, a fluorophore, a quencher, a calibrant, a tagged reagent, or a combination thereof. A tagged reagent may be, for example, an antibody, peptimer, aptamer, or other capture molecule that contains one or more of a fluorescent tag, a quencher (e.g., dimethylaminoazobenzenesulfonic acid), or combination thereof. Tagged reagents could also be pre-loaded onto biomarkers of interest or immobilized onto the device. For example, a detection platform could utilize a cyan fluorophore, such as cyan fluorescent protein (CFP), tethered to a primary antibody and a yellow fluorophore, such as yellow fluorescent protein (YFP), tethered to a secondary antibody capable of recognizing the analyte. In an embodiment, the primary antibody may be immobilized on a surface of the channel 12, and the osmotic flow would deliver the secondary antibody from the draw solution 20 into the channel 12. Analogous to an enzyme-linked immunosorbent assay (ELISA), the antibody-analyte-antibody sandwich would form if sufficient analyte is present in the fluid sample. Only upon formation of the sandwich would fluorescence resonance energy transfer (FRET) be observed, where excitation of CFP would result in emissions from YFP. FRET is an established technique to those with knowledge in the art, but an aspect of the present invention is the ability to specifically add controlled concentrations of fluorophore and fluorophore-tagged reagents in real-time to a sample fluid. In an embodiment using an optical reaction, the optical detection may be along the length of the channel to provide a relatively long optical path length.

Further, an embodiment may include a reagent in a dissolvable material in the flow path of the fluid sample. As the sample flows over the dissolvable material, the material begins dissolving and releasing the reagent into the sample fluid. In this manner, more than one reagent with differing molecular weights can be introduced to the fluid sample at the same rate. Furthermore, a second species of reagent, which always absorbs light or fluoresces, could be introduced to account for unknown dilution (dissolution rate, incoming flow rate) and ratios of fluorescent or absorption signals could be measured to obtain quantitative results.

Figure 2:
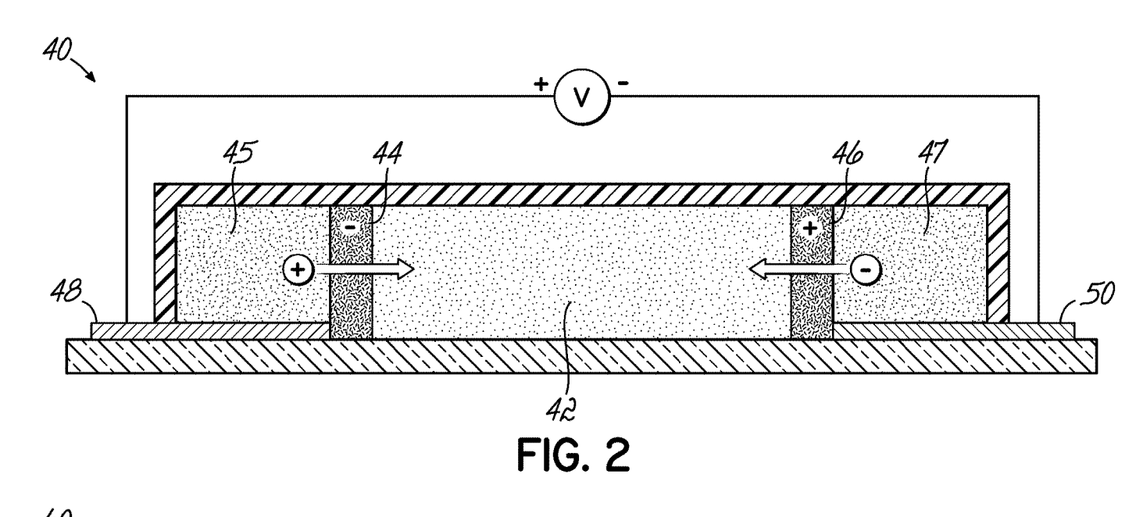
FIG. 2 is a schematic cross-sectional view of a device according to an embodiment of the disclosed invention capable of salinating or buffering a biofluid sample.

With reference to FIG. 2, in an embodiment, a device 40 includes using electrophoresis to deliver a compound to the fluid sample. Electrophoresis is the movement of charged molecules when an electric field is applied. This process delivers charged reagents to a fluid sample. The process allows for functions including, but not limited to, changing pH, adding enzymes, adding salts, and preparing for an assay. In FIG. 2, fluid flows through a channel 42 having sidewalls 44, 46 separating reservoirs 45, 47. The top and bottom of the channel 42 may be, for example, PET and glass. In the exemplary embodiment, sidewalls 44, 46 of the fluid channel 42 are made of polyacrylamide (PAM) or PAM modified by the addition of charged components. PAM is a hydrogel, enabling water and ion flux but providing a significant barrier to the bulk of the fluid. PAM may be cast in high concentrations (e.g., 1-40%) to enable it to act as a semipermeable membrane, which retards the flow of analytes of interest into the PAM layers 44, 46. For example, the sidewall 44 may be made of negatively charged PAM, and the sidewall 46 may be made of positively charged PAM. When the PAM is charged, it is difficult for salt to diffuse back into the channel 42 until voltage is applied via electrodes 48, 50, which contact the sidewalls 44, 46, respectively.

Aptamers and enzymes intrinsically have a charge to them, negative in the former case, and either negative or positive in the latter case. As a result, aptamers (negatively-charged) can be selectively and controllably delivered into the sample stream using an applied voltage. A positively-charged PAM layer (e.g., layer 46) permits the passage of the aptamer into the fluid channel. To prevent the aptamer from migrating to the counter-electrode (e.g., electrode 48) outside of the sample stream, negatively-charged PAM layer (e.g., layer 44) has sufficiently low porosity to deter the passage of the aptamer out of the fluid channel and toward the counter-electrode. This configuration enables sandwich assays that rely on radiometric, fluorometric, or colorimetric outputs. A similar configuration could be used for enzyme delivery, peptimer delivery, antibody delivery, or reagent delivery. As described below, the PAM layer may separate the fluid channel from a fluid reservoir to allow for a bath of the desired reagent to enable continuous operation.

Figure 3:
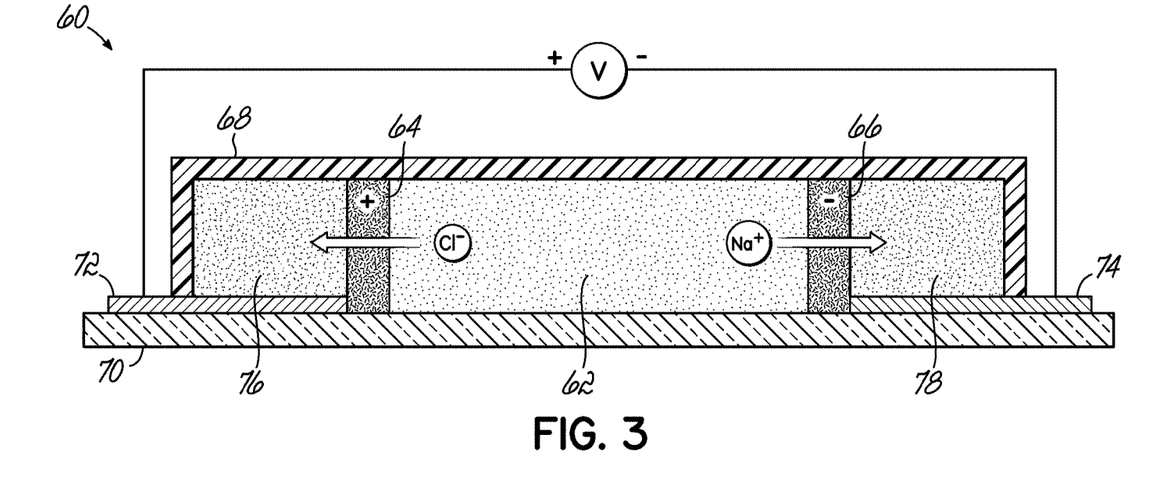
FIG. 3 is a schematic cross-sectional view of a device according to an embodiment of the disclosed invention capable of desalinating a biofluid sample.

With reference to FIG. 3, in an embodiment, a device 60 uses electrodialysis to desalinate a sample and buffer the pH. Removing salts from a sample is important in water treatment, biofluid analysis, and chemical processing applications. In FIG. 3, a fluid channel 62 includes sidewalls 64, 66 and top 68 and bottom walls 70. In the exemplary embodiment, sidewalls 64, 66 of the fluid channel 62 are made of polyacrylamide (PAM), which may or may not be charged. Ions can be withdrawn from the sample using iontophoresis by applying an electric current through two electrodes 72, 74 positioned on either side of the PAM layers. Opposite the sidewalls 64, 66 from the channel 42 can be a fluid reservoir or channel 76, 78 to contain the withdrawn ions, which in some cases can be at a concentration much lower than the sample stream in order to make desalination thermodynamically favorable and thus reduce the required energy.

Figure 4A:
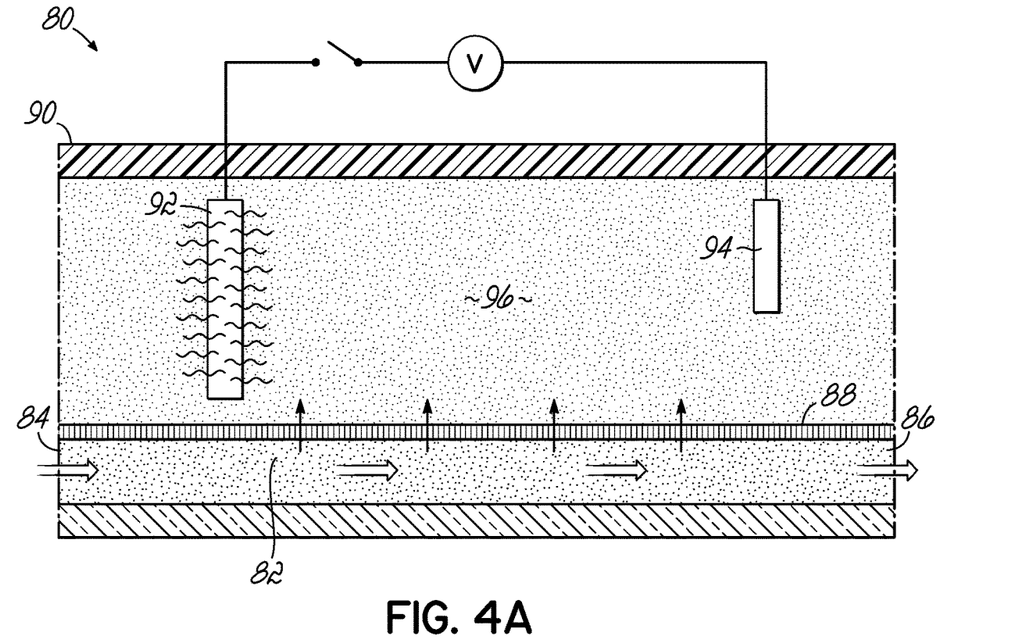
FIG. 4A is a schematic cross-sectional view of a device according to an embodiment of the disclosed invention capable of controlling the change in concentration of a draw solution.
Figure 4B:
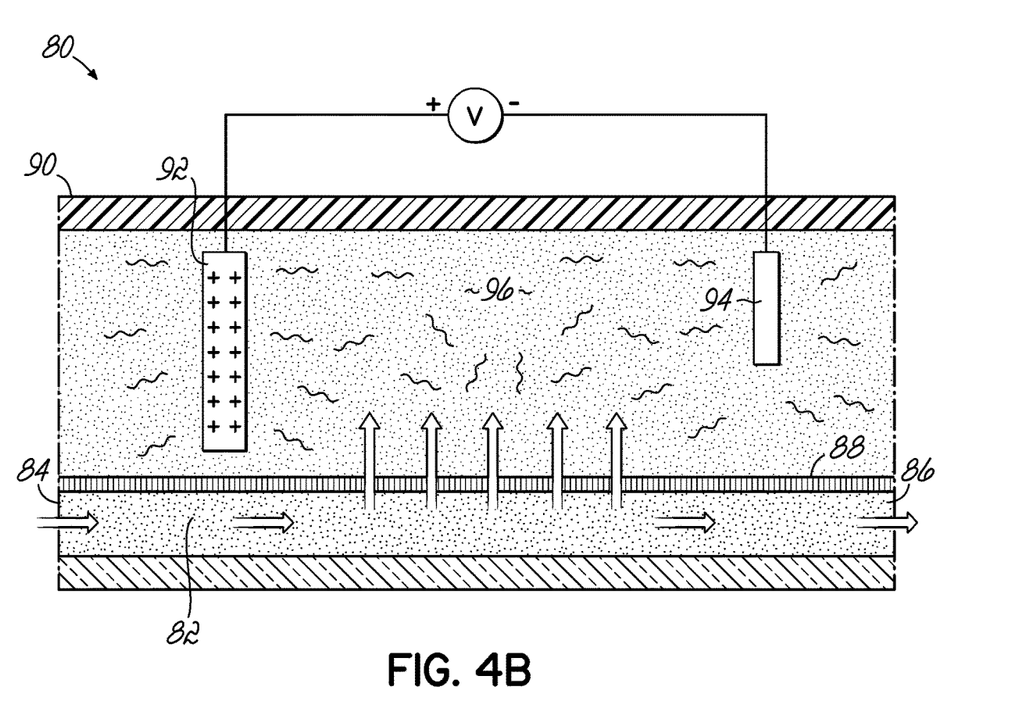
FIG. 4B is a schematic cross-sectional view of the device of FIG. 4A after a voltage has been applied.

Embodiments of the disclosed invention are directed to controlling osmolarity by applying an electric field. One method to control a change in concentration is through redox reactions. In an embodiment, with reference to FIGS. 4A and 4B, a device 80 includes a fluid channel 82 with an inlet 84, and outlet 86, and a semipermeable membrane 88 as one of the sidewalls of the channel 82. Exemplary semipermeable membranes include membranes comprised of polyethersulfone, cellulose acetate, polycarbonate, polyamide, polyimide, polysulfone, polyethylene, polypropylene, polyacrilonitrile, polyvinylidiene fluoride, polyvinyl chloride, and combinations thereof. The semipermeable membrane 88 separates the channel 82 from a chamber 90 containing two electrodes 92, 94 in a draw solution 96. In solution, gold in an electrode 92 spontaneously bonds to thiol groups under no electric field, creating gold(I) thiols. However, as shown in FIG. 4B, these can be released upon application of a reductive potential (e.g., about −0.4 V vs Ag/AgCl), undergoing the following reaction:

$$Au\text{—}S\text{—}R + H\text{—}O\text{—}H + e^- \rightarrow Au(s) + R\text{—}SH + {}^-OH$$

This process generates two molecules per electron. The counter electrode 94 could be designed in such a way to undergo an oxidation reaction, such as:

where the $^-$OH is attracted to the X$^+$ creating a capacitor and sequestering the ion. X can be any redox marker, such as ferrocene, methylene blue, or other redox indicators known to the those skilled in the art, that goes from a neutral to a positively charged state upon application of an oxidation potential. Thus, for every electron transfer, a molecule is released into solution, increasing the osmolarity of the draw solution 96. Changing the osmolarity of the draw solution 96 affects the modulation of the sample flowing through the channel 82. For example, a higher osmolarity of the draw solution 96 causes water and/or solutes to flow from the sample into the chamber 90.

In another embodiment, the anode could be made of a conducting polymer including but not limited to poly(3,4-ethylenedioxythiophene) (PEDOT) or poly(pyrrole)s (PPY). Upon application of an oxidative potential, the PEDOT would be oxidized, generating a positively charged surface that would attract a negative ion such as chloride to the surface. This effectively creates a capacitor, while simultaneously effectively removing an anion from the solution. The cathode in this instance would also be redox sensitive, such as a chlorinated polymerized benzoquinone, that at neutral pH would have a negative charge upon reduction (e.g., chlorinated polymerized benzoquinone being reduced to hydroquinone). In such a case, the positive ion, such as sodium, would be attracted to the surface creating a capacitor, again removing ions from solution and reducing the osmolarity.

In both of these cases, application of voltage and the subsequent redox reactions modulate the osmolarity of the draw solution, enabling control of the osmolarity of the draw solution as a function of voltage and current. In addition, the method would be immensely useful in a device that has multiple sensors with different level of detections and ranges.

Figure 5:
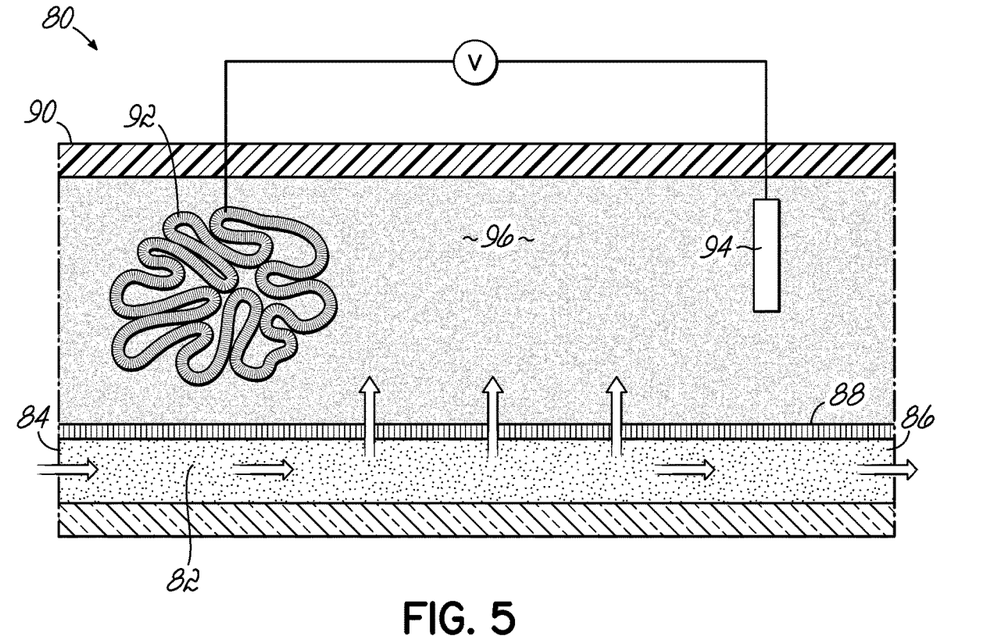
FIG. 5 is a schematic cross-sectional view of a device according to an embodiment of the disclosed invention showing an alternative electrode configuration compared to FIG. 4A.

With reference to FIG. 5, which is a modification of the embodiment illustrated in FIG. 4, for high concentration levels inside the draw solution to be achieved, the electrode 92 may be a high surface area electrode that will allow for a high density of thiol groups per unit volume. Suitable high surface area electrodes include ultracapacitors, surface treated electrodes (including but not limited to gold nanorods), or porous electrodes (including but not limited to porous conducting polymers).

Figure 6:
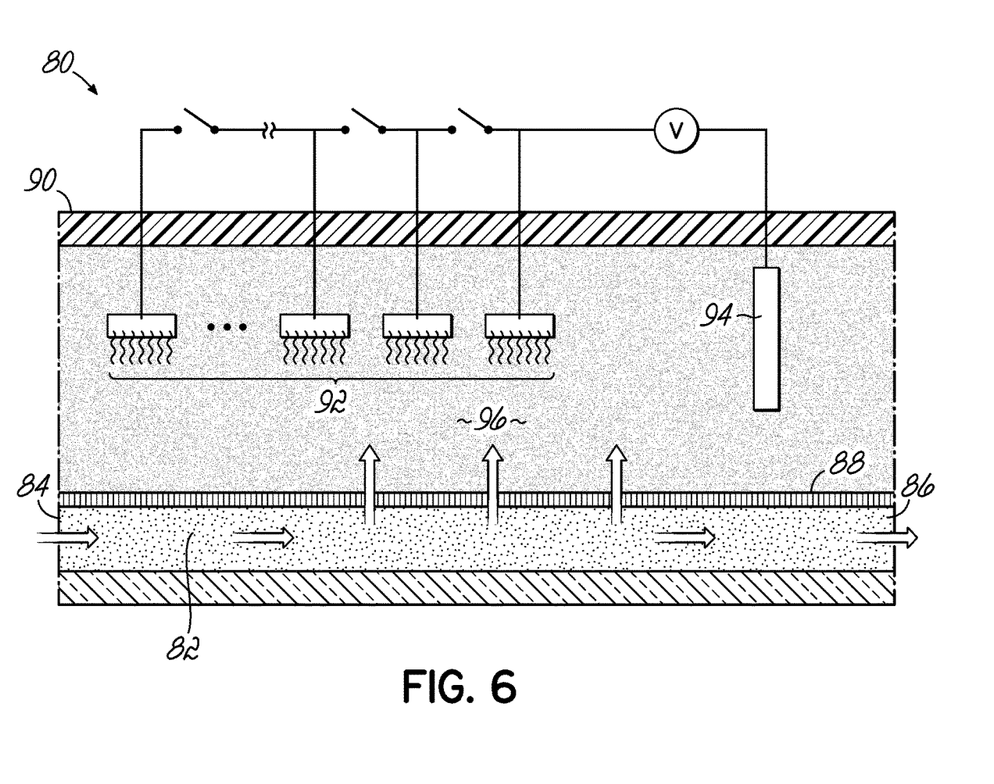
FIG. 6 is a schematic cross-sectional view of a device according to an embodiment of the disclosed invention showing an alternative electrode configuration compared to FIG. 4A.

With reference to FIG. 6, which is a modification of the embodiment illustrated in FIG. 4, concentration level inside the draw solution can be a discretely adjusted between some low and high value by cascading n number of electrodes 92 with a fixed amount of thiols for each electrode 92. Each electrode 92 could independently apply an electric field that results in the release of thiols. For example, ten gold electrodes could be used as anodes and cathodes, and n could be selectively activated to release n/10$^{th}$ of the total reagent into solution, enabling precise and predictive concentration change.

In an aspect of the disclosed invention, processing functions can be combined in parallel. Positioning two or more processing functions within the same module has multiple advantages. In applications where space is limited, such as processing biofluids in vivo, a combined approach is more compact. In some applications, the delay between input and output—the latency—is critical to minimize. For example, latency may be a concern when measuring biomarkers like glucose where an action must be taken within a short amount of time in response to rapid changes. A combined approach makes it possible to shorten the total latency for these applications.

Figure 7:
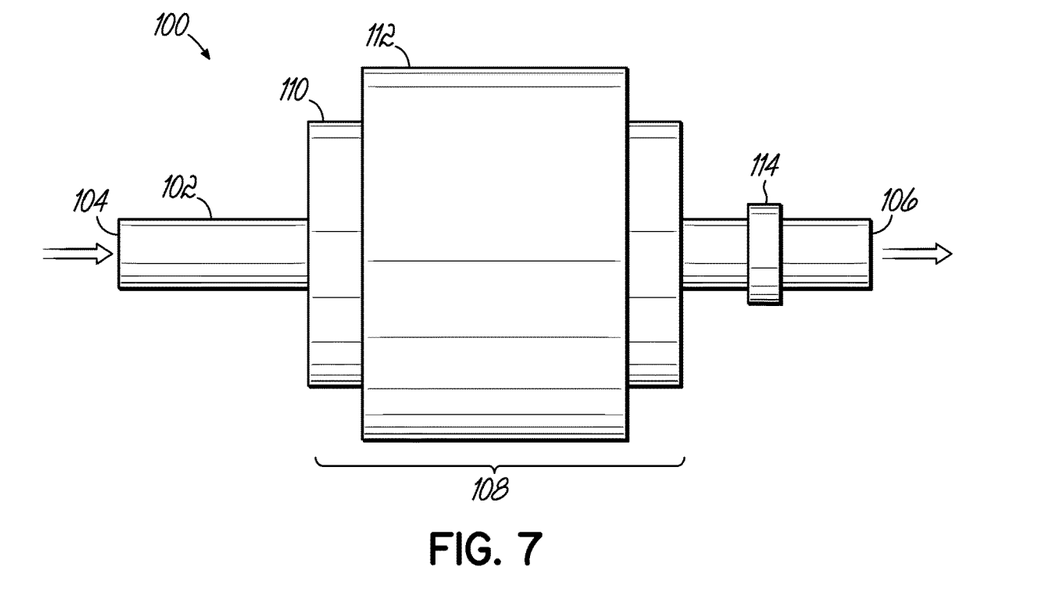
FIG. 7 is a schematic view of a device according to an embodiment of the disclosed invention that includes one module with parallel processing components.

With reference to FIG. 7, in an embodiment, a device 100 with parallel components includes a fluid channel 102 having an inlet 104 and an outlet 106. Within the fluid channel 102 is a processing module 108 made up of two sample-modulating components 110, 112. The module 108 may include more than two components. When a fluid sample flows through the module 108, the functions of the two sample-modulating components 110, 112 are performed simultaneously. Various components that may be combined may perform a variety of functions. Examples of the module functions follow. The sample may be concentrated to increase a concentration of a component or analyte in the sample by at least 1.5×. The sample may be diluted to decrease a concentration of a component or analyte in the sample by at least 25%. The sample may be desalinated to decrease a concentration of salt in the sample by at least 10%. The pH of the sample may be adjusted to bring the pH into a predetermined range. One or more non-polar substances may be absorbed to decrease the concentration of the non-polar substances by at least 2×. One or more reagents may be delivered to the sample to provide a desired concentration of the reagents in the sample. In FIG. 7, a sensor 114 is shown positioned downstream from the module. A sensor can be added upstream from, in, or downstream from the module. In cases where the fluid is being modified by the module 108 for downstream use, sensors may not be needed.

Figure 8:
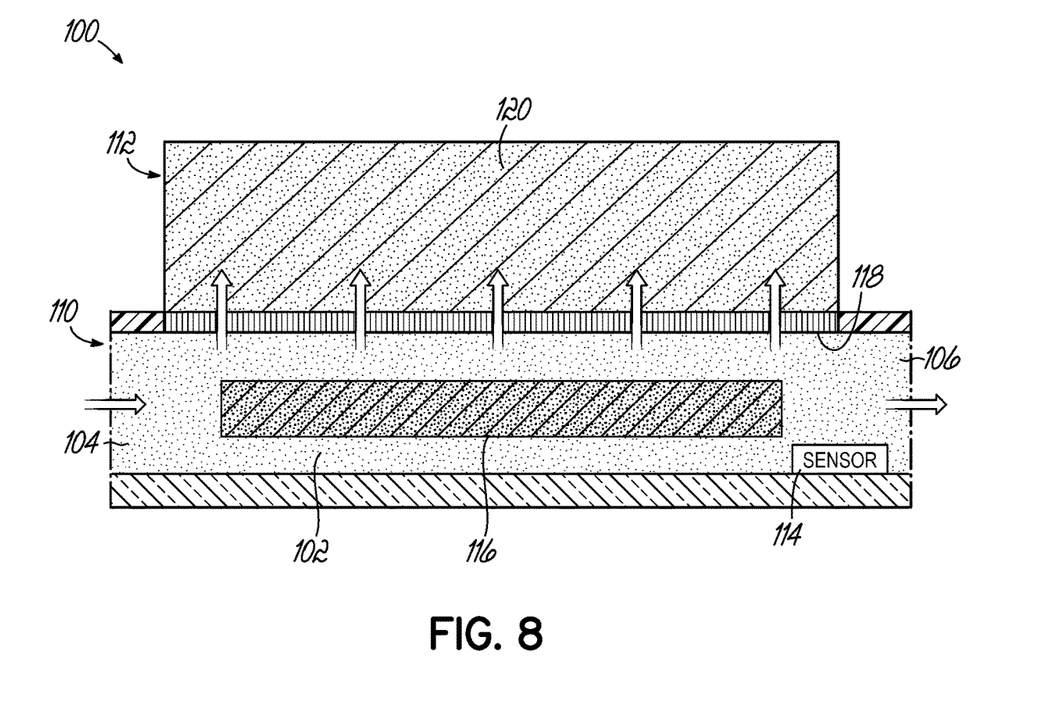
FIG. 8 is a schematic cross-sectional view of the module and sensing component of FIG. 7 according to an embodiment of the disclosed invention.

With reference to FIG. 8, an example configuration of the module 108 is shown. In an embodiment, the component 110 removes lipids and hormones through use of a resin 116, and the component 112 concentrates the biofluid. Removal of lipids and hormones may be needed for biosensors such as aptamers, antibodies, and enzymatic biosensors. The removal of these non-polar substances is accomplished by absorption into a resin 116 that is fixed within the fluid path. In another embodiment, a surface of the channel 102 (e.g., a section of the bottom, top, or sidewalls) is made of a material that absorbs non-polar substances. Concentration of the biofluid is accomplished using osmosis. A semipermeable membrane 118 separates the biofluid from a draw solution 120. Water flows from the biofluid sample into the draw solution 120 with a higher osmolarity. As an example, the draw solution contains 2000 Osmoles (i.e. 1M NaCl solution) and the biofluid equivalent to 200 Osmoles would cause water to flux across the membrane from the sample until equilibrated to 2000 Osmoles. The fluid path can be made sufficiently long so that the by the end of the fluid path, enough water has fluxed from the sample into the draw solution 120 to be at equilibrium with the draw solution 120. The modified, concentrated biofluid then passes across a sensor 114 (shown in FIG. 7) for measuring a specific analyte (e.g., glucose, salts, protein, etc.).

Figure 9:
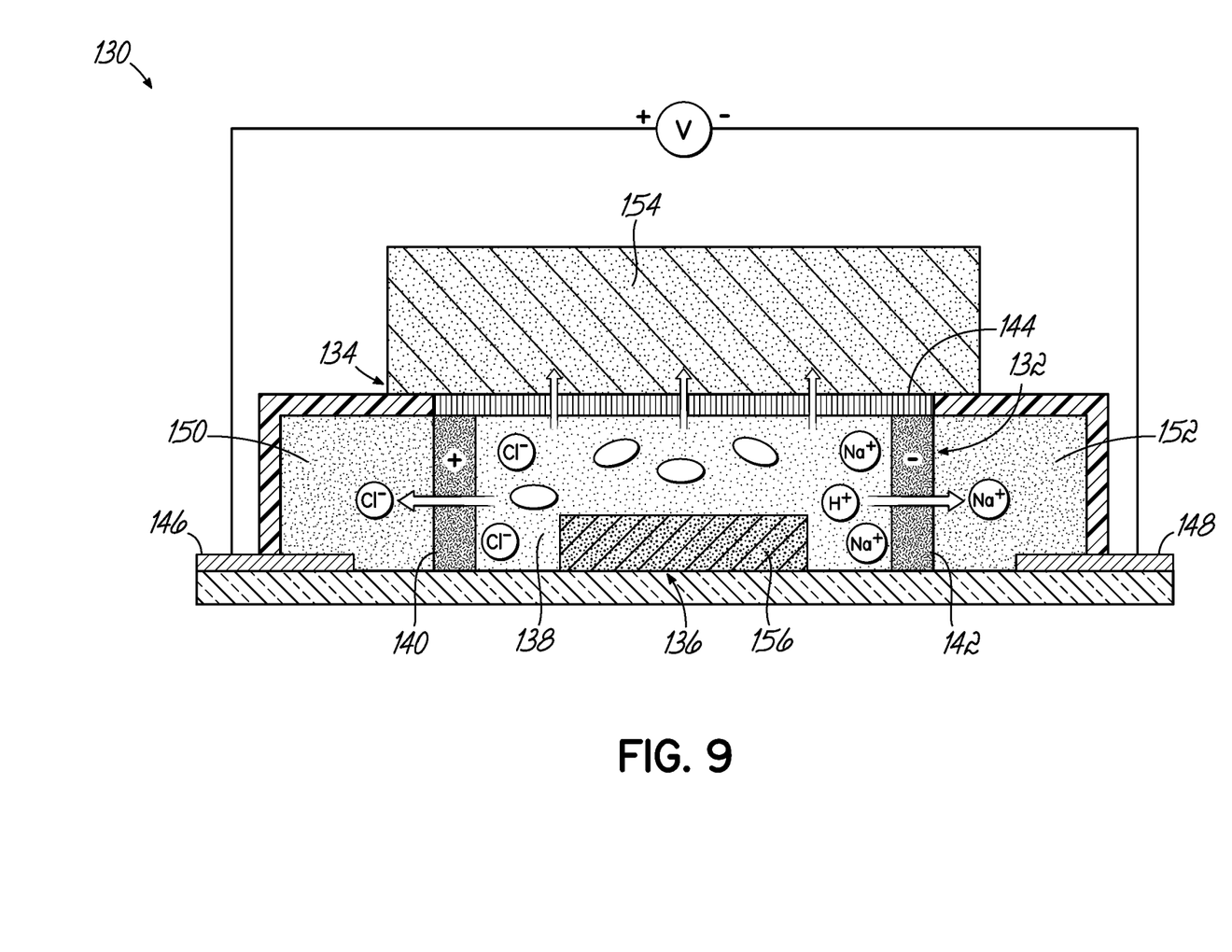
FIG. 9 is a schematic cross-sectional view of a device according to an embodiment of the disclosed invention that includes three processing components in parallel.

With reference to FIG. 9, in an embodiment, a single processing module 130 includes three components 132, 134, 136 that each perform a specific function. The three components are in parallel (i.e., the functions happen simultaneously). The fluid being modulated flows through a fluid channel 138, which includes sidewalls 140, 142 and a semipermeable membrane 144. The first component 132 desalinates the sample using electrodialysis. In order to accomplish this within the fluid path, the sidewalls 140, 142 of the fluid channel 138 can be made of, for example, PAM or PAM modified by the addition of charged components.

When a charge is introduced, the PAM can act as an ion-exchange resin/ion-selective membrane analogous to those observed in conventional electrodialysis devices. The advantage to using PAM over a traditional membrane is the ability to drop-cast the PAM into any dimension. Ions can then be withdrawn from the fluid using electrophoresis by applying an electric current through two electrodes 146, 148 positioned on either side of the PAM layers 140, 142. To enable greater capacity to desalinate and to improve thermodynamics, the PAM layers 140, 142 may separate the channel 138 from fluid reservoirs 150, 152 to collect the withdrawn ions at an osmolarity lower than that desired in the sample.

Still referring to FIG. 9, the second component 134 concentrates the sample using osmosis. The semipermeable membrane 144 separates a highly osmotic draw solution 154 from the sample. The semipermeable membranes may consistent of different materials (e.g. polyethersulfone, cellulose triacetate, polycarbonate) and pore sizes (>1 Da). Membranes materials may be hydrophilic or hydrophobic in nature. If hydrophilic, they may be charged or uncharged. Membranes may be selected to have surface chemistries that prevent loss of analytes by surface binding, improving recovery. The pore size of the membrane determines the minimum size of the draw molecule. Small pores size (<150 Da) limit the draw to salts (NaCl), mid-sized pores (150-300 Da) allow for sugars (e.g., glucose, sucrose) to be used, and large-size pores (>300 Da) allow for polymers and polyelectrolyte draw molecules to be used (e.g., polyethylenimine) While the first component 132 was placed within the sidewalls 140, 142 of the channel 138, the second component is positioned outside of and adjacent to the channel 138. The membrane 144 is selected to prevent the transfer of analytes of interest while allowing sufficient water flux through the membrane 144 to allow osmosis to drive the flux of water from the sample into the draw solution 154. As water is removed from the sample, the sample becomes more concentrated. The fluid path is designed to be long enough to allow the sample to reach equilibrium with the draw solution 154. The draw solution 154 is sufficiently large so the change in concentration due to the flux of water into the solution 154 will cause negligible impact on its osmolarity. As a result, the total amount of concentration is roughly the same as the ratio of the osmolarity of the draw solution 154 to the initial osmolarity of the sample.

Still referring to FIG. 9, the third component 136 removes nonpolar substances (e.g., lipids and hormones) via absorption into a fixed resin 156 found within the fluid channel 138. As concentration of the biofluid sample goes from 10× to 100× to 1000×, lipids are likely to perturb the binding of the biomarkers of interest and even to denature the biomarkers of interest, which may prevent detection. Polystyrene beads (e.g., Biobeads from BioRad) and other hydrophobic resins are known to be absorbed by detergents or resins due to van der Waals forces.

Advantages of devices using two or more sample-modulating components include the ability to control the degree of concentration by varying the voltage and the applied current and also to remove interfering agents such as lipids and salts. The number of ions removed directly correlates to the total number of electrons passed through the circuit. As more ions are removed, the osmotic gradient increases, leading to osmotic flux. Thus, the degree to which an analyte is concentrated is at least partially dependent on the applied voltage, current, and time of applied current is applied. Additionally, the salinity within the sample can be controlled during the concentration process. For example, to obtain $100x$ concentration of a sample in a device including only two components, salt would either have to be removed from a 100 mM sample to 1 mM using a membrane-based approach or the salinity would have to increase to 10 M. In either case, biomolecules will become unstable and likely precipitate out. The other additional benefit is that pH is also modulated electrophoretically, as $OH^-$ and $H^+$ ions have high electrophoretic flux due to their small size, and thus will be preferentially removed until the pH is 7 (i.e., $[OH^-]=[H^+]$).

Finally, in addition to desalinating, concentrating, and absorbing nonpolar substances as described above, the components could be substituted to perform other functions such as concentrating/diluting, adjusting pH, or delivering reagents.

Figure 10:
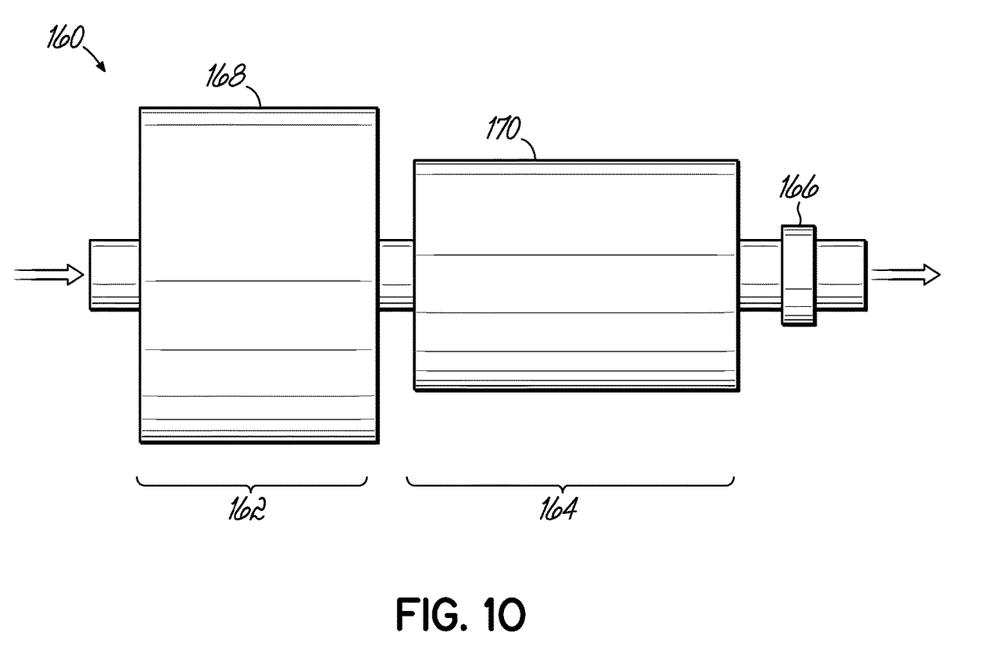
FIG. 10 is a schematic cross-sectional view of a device according to an embodiment of the disclosed invention that includes two processing modules in parallel.

In an aspect of the disclosed invention, a device may include more than one module where, for example, the processing steps cannot be done in a single step. For example, it may be necessary to remove interfering components like lipids from a sample prior to subsequent steps that may be susceptible to fouling by lipids (e.g., a membrane filtration step). With reference to FIG. 10, a device 160 includes two modules 162, 164 in series that prepare a sample prior to exposure to a sensor 166. While each of the modules 162, 164 are shown as having one sample-modulating component 168, 170, it should be recognized that the modules 162, 164 may have more than one component.

In another aspect, sets of components and sensors can also be combined in series. For example, biosensors have different sensitivities, and the biomarkers they measure are found at different concentrations. Consequently, each biosensor would best sense the sample when the sample is concentrated or in some cases diluted to a specific concentration. A non-limiting exemplary embodiment includes three biosensor/biomarker combinations. Based on the physiological concentration of the sample and the working concentration range of the biosensor, each biosensor performs best if the concentration was 10×, 100×, and 1000×, respectively. Three modules may be positioned in a series, with each module including a processing component and a sensor downstream from its corresponding component. The component of the first module in the series concentrates the sample to 10×, which allows the first sensor to sense the first biomarker of interest. Then, the sample flows through the second module in which the 10× concentrated fluid is further concentrated another 10× to bring the total concentration to 100× thereby allowing the sensor in the second module to sense the second biomarker of interest. The third module increases the concentration to $1000x$ allowing the third sensor to sense the third biomarker of interest. It should be recognized that modules in series may each include one or more components functioning in parallel as described herein. For example, each component within a module can have functions including buffering pH, delivering reagents, and diluting.

Figure 11:
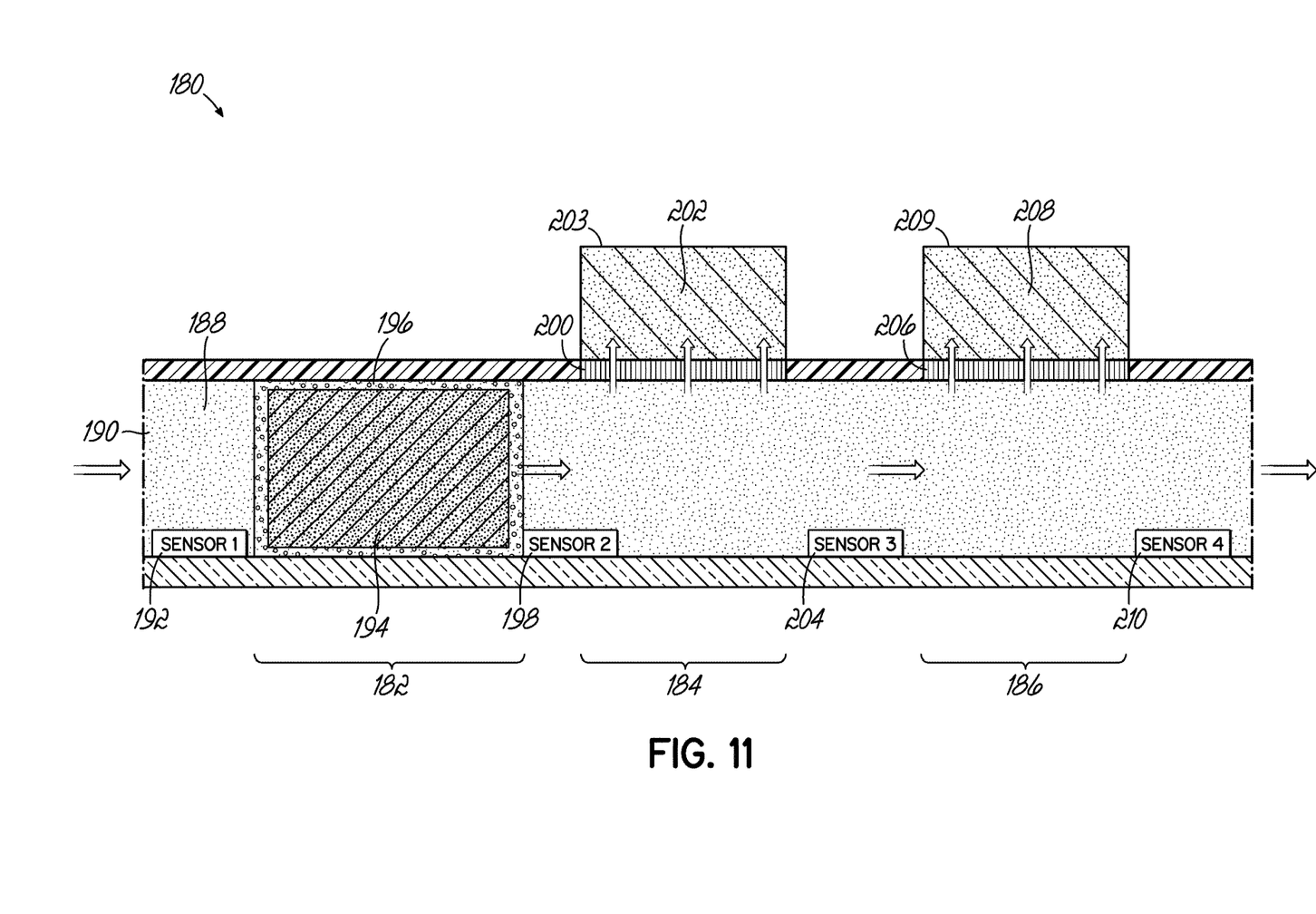
FIG. 11 is a schematic cross-sectional view of a device according to an embodiment of the disclosed invention that includes three processing modules in parallel, each module including a processing component and a sensor.

With reference to FIG. 11, in an embodiment, a device 180 includes three modules 182, 184, 186 in series. First, the sample of biofluid enters a channel 188 through an inlet 190 and is transported across a sensor 192 that measures the concentration of an analyte, such as chloride, in the initial sample. Next, the sample flows into the first module 182. The first module 182 includes two components performing the parallel functions of (1) nonpolar substances (e.g., lipid and hormone) absorption and (2) desalination of the biofluid. The removal of these nonpolar substances is accomplished by absorption of the substances into a resin 194 that is fixed within the fluid path. The desalination of the biofluid is accomplished via flow through ion-exchange resin fixed in place by a hydrogel 196 (e.g., a layer of PAM). Removal of excessive salts, lipids, and hormones generates better operating conditions for aptamers, antibodies, and enzymatic biosensors. At the end of the first module 182, the fluid passes across another chloride sensor 198. By comparing the final chloride concentration and the initial chloride concentration, the level of desalination can be determined, which will directly impact the degree of concentration from the second and third modules 184, 186. The sample is then transported into the second module 184.

Still referring to FIG. 11, the second module 184 allows for the concentration of the sample to a level of detection for some proteins or hormones (e.g., albumin) using a semipermeable membrane 200 and a draw solution 202 (e.g., solutions including sugars such as glucose, fructose, and/or sucrose; polyelectrolytes such as polyethylenimine; and/or salts such as NaCl, KCl, or MgCl) in reservoir 203. The ranges for the draw solution would be >150 Osmoles, which depends on the sample concentration (typically 100 Osmoles) and depending on the desired final concentration. The final desired volume of the sensor and the amount of available fluid also determines the concentration possible. For example, if an assay or sensor requires 1 mL of solution and a 100x concentration is desired, the starting solution would need to be 1 L of solution. Water flows from the sample through the semipermeable membrane 200 into the draw solution 202, which has a higher osmolarity than the sample that is generated by the amount of solute in the draw solution 202. At the end of the second module 184, the sample is sensed using an aptamer-based sensor 204. The sample is then transported into the third module 186. The third module 186 includes another semipermeable membrane 206 and draw solution 208 in reservoir 209 that increases the sample's concentration to allow for the detection of, for example, glucose using an enzymatic biosensor 210. In addition to desalting, concentrating, and lipid and hormone absorption with resin that are described above, the components within the modules could be substituted for those that perform concentrating/diluting, adjusting pH, absorbing other nonpolar molecules, or delivering reagents.

In an aspect of the disclosed invention, controlling the extent of certain processing steps is useful in achieving precise sample conditions. To accomplish this, a feedback loop may be used. Feedback consists of inputs and outputs. The inputs to a feedback system include data acquired by one or more sensors. Sensors provide information regarding the condition of the sample during processing and can include analyte-specific sensors, flow rate sensors, and pressure sensors. The outputs are mechanical or electrical methods of adjusting the processing of samples or altering the fluid path. Accordingly, sample preparation conditions may be altered in real-time based on measured sample conditions. Sensors are monitored through software/microprocessor or through a user/operator capable of manually adjusting sample preparation conditions.

Figure 12:
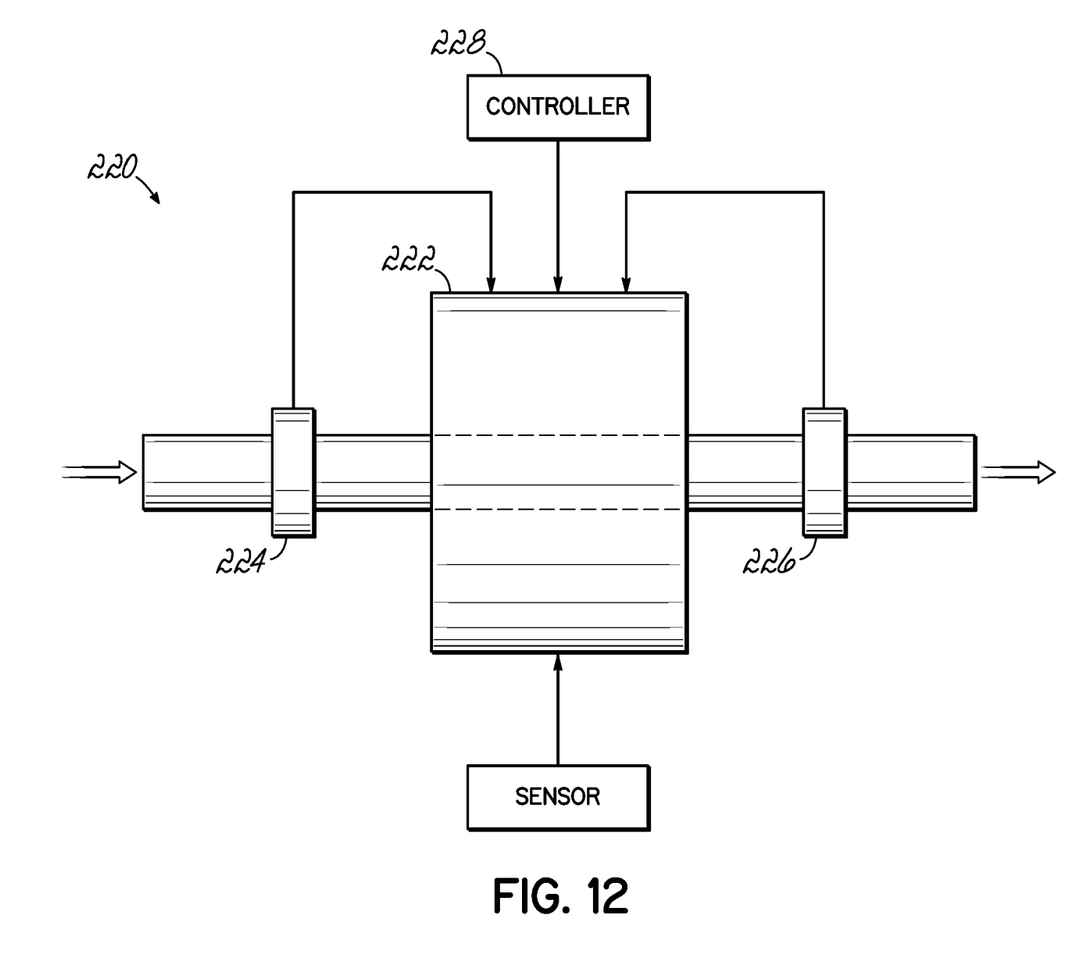
FIG. 12 is a schematic cross-sectional view of a device according to an embodiment of the disclosed invention showing the use of feedback for controlling the extent of certain processing steps.

With reference to FIG. 12, in an embodiment, a device 220 includes a sample-modulating component 222 that concentrates a sample using electrodialysis. Sensors 224, 226 are positioned upstream and downstream, respectively, from the component 222. In an embodiment, a feedback loop determines whether the analyte is in a concentration range able to be detected by the analyte-specific sensor (not shown). In an embodiment, a controller 228 may be configured to control the application of voltage in the electrodialysis component 222. Sensors used for feedback can be placed in the fluid stream before, during, or after the module or may be external to the sample stream. Feedback sensors may measure a general property of the sample stream or of the process conditions (e.g., sense ambient temperature) or could be analyte-specific. If the analyte concentration is too low for detection by the biosensor, the applied voltage can be increased, and thus the degree of concentration is increased. If the analyte concentration is too high, then the applied voltage can be decreased to reduce the extent of concentration. In such a way, the concentration can be optimized to fit the downstream requirements of the desired sensor.

Figure 13:
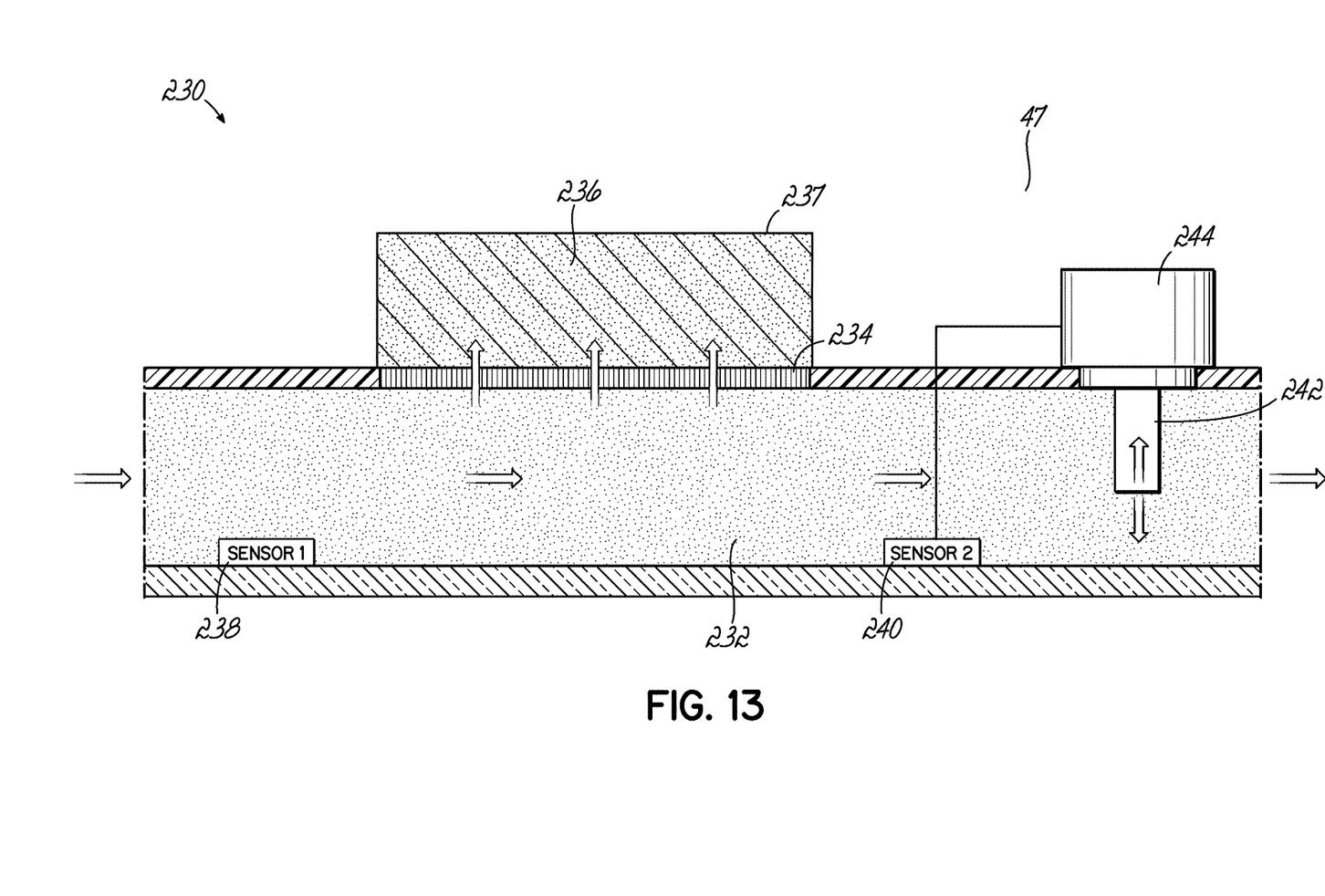
FIG. 13 is a schematic cross-sectional view of a device according to an embodiment of the disclosed invention showing the use of feedback for controlling the extent of certain processing steps.

With reference to FIG. 13, in an embodiment, a sample-modulating component 230 concentrates a sample in a microfluidic channel 232 using a semipermeable membrane 234 and a draw solution 236 in reservoir 237. The first sensor 238 monitors the concentration of analyte at the inlet of the component 230, and the second sensor 240 monitors the concentration of the analyte after the sample is processed by the component 230. An electronically controlled gate 242 is located downstream and is able to control the flow rate of the sample in the channel. The gate 242 is controlled using an electronic switching system 244 that may include, but is not limited to, a microcontroller, a microprocessor, or a computer. The feedback is designed such that, when the concentration reading at the second sensor 240 falls below or above a particular concentration, the gate 242 is closed or opened so that the sample remains under the membrane 234 for more or less time, respectively.

While specific embodiments have been described in detail to illustrate the disclosed invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A device for preparing a fluid sample comprising:
a sample-modulating component capable of delivering one or more reagents to the fluid sample by osmotic flux to provide a desired concentration of the one or more reagents in the sample, the sample-modulating component comprising a membrane separating a reservoir from a channel, the reservoir configured to house the one or more reagents, and the membrane configured to allow passage of the one or more reagents from the reservoir to the channel, wherein the osmotic flux includes transporting the one or more reagents from the reservoir to the channel by way of an applied pressure on the one or more reagents; and
an analyte-specific sensor for measuring an analyte in the sample.

2. The device of claim 1, wherein the one or more reagents include at least two solutes, the at least two solutes configured to be delivered to the sample at a ratio, and the ratio of the at least two solutes is measured to give a quantitative measurement.

3. A method of processing a fluid sample comprising:
collecting the fluid sample;
flowing the fluid sample through a sample-modulating component, the sample modulating component comprising a reservoir, a channel, and a membrane separating the reservoir from the channel;

delivering one or more reagents, housed in the reservoir, to the sample by osmotic flux by applying a pressure on the one or more reagents to provide a desired concentration of the one or more reagents in the sample to form a modulated sample; and measuring an analyte in the modulated sample using an analyte-specific sensor.

\* \* \* \* \*